(12) United States Patent
Schäfer et al.

(10) Patent No.: US 6,534,615 B2
(45) Date of Patent: Mar. 18, 2003

(54) PREPARATION OF AMINO-FUNCTIONAL SILOXANES

(75) Inventors: Oliver Schäfer, München (DE); Volker Frey, Burghausen (DE); Bernd Pachaly, Mehring-Öd (DE); Andreas Bauer, München (DE)

(73) Assignee: Consortium fur Elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/971,437

(22) Filed: Oct. 5, 2001

(65) Prior Publication Data

US 2002/0049296 A1 Apr. 25, 2002

(30) Foreign Application Priority Data

Oct. 19, 2000 (DE) .......................................... 100 51 886

(51) Int. Cl.⁷ ...................... C08G 77/26; C08G 77/06; C08G 77/388; C07F 7/20
(52) U.S. Cl. .......................... 528/38; 528/33; 528/37; 556/407; 556/410; 556/412; 556/413; 556/425
(58) Field of Search .............................. 528/33, 37, 38; 556/407, 410, 412, 413, 425

(56) References Cited

U.S. PATENT DOCUMENTS

| 3,146,250 | A |   | 8/1964  | Speier          |         |
|-----------|---|---|---------|-----------------|---------|
| 4,499,234 | A | * | 2/1985  | Pratt et al.    | 524/783 |
| 4,584,393 | A |   | 4/1986  | Webb et al.     |         |
| 4,981,988 | A | * | 1/1991  | Ichinohe et al. | 556/425 |
| 5,118,777 | A | * | 6/1992  | Okawa           | 528/34  |
| 5,162,560 | A | * | 11/1992 | King et al.     | 556/445 |
| 5,512,650 | A |   | 4/1996  | Leir et al.     |         |

FOREIGN PATENT DOCUMENTS

| DE | 35 46 376 A1  |   | 7/1986 |              |
|----|---------------|---|--------|--------------|
| DE | 4234846 A1    | * | 4/1994 | C08G/77/388  |

OTHER PUBLICATIONS

Derwent Abstract Corresponding to DE 35 46 376 [AN 1986–125089].

\* cited by examiner

Primary Examiner—Robert Dawson
Assistant Examiner—Jeffrey B. Robertson
(74) Attorney, Agent, or Firm—Brooks & Kushman P.C.

(57) ABSTRACT

The invention relates to a process for preparing an amino-functional organosiloxane of the formula III,

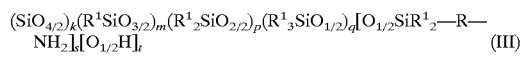

which comprises reacting an organosiloxane of the formula IV

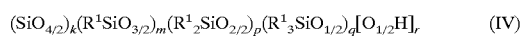

with a cyclic silazane of the formula V

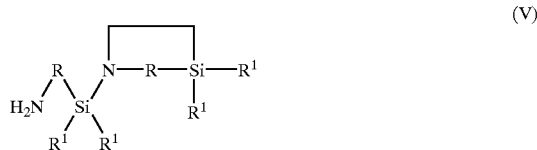

where
R, $R^x$, $R^1$, s, t, r, k, m, p and q are as defined in claim 1.

10 Claims, No Drawings

PREPARATION OF AMINO-FUNCTIONAL SILOXANES

BACKGROUND OF THE INVENTION

1. Field of the Invention

The invention relates to a process for preparing amino-functional siloxanes using cyclic silazanes. Aminoalkylpolysiloxanes and aminoalkyl silicone resins can be used in many fields, including the preparation of polyimides and polyetherimides. However, the commercial use of these compounds on a large scale is hindered by a relatively expensive production process.

2. Background Art

A known process for the preparation of amino-functional siloxanes is the base-catalyzed equilibration of octamethylcyclotetrasiloxane with bisaminopropyltetramethyldisiloxane, as described, for example, in U.S. Pat. No. 5,512,650. This reaction has the disadvantage that expensive bisaminopropyltetramethyldisiloxane is used as starting material. In addition, the long reaction times required by the equilibration reaction, sometimes more than 10 hours, are disadvantageous.

U.S. Pat. No. 3,146,250 describes a further process which has hitherto not been employed industrially and begins with from specific cyclic silanes of the formula I which can react with HO—Si groups at the end of a silicone chain.

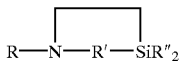

(I)

In this formula, R' is a carbon chain having at least 3 and not more than 6 carbon atoms, R" is a hydrocarbon radical, and the radical R on the nitrogen is either hydrogen, a hydrocarbon radical or an organosilyl radical of the formula (halogen-$R^1$—) $Y_2Si$—, where Y and $R^1$ are hydrocarbon radicals. If the radical R is hydrogen, the compound is an unsubstituted cyclic silazane which can be used for functionalizing hydroxy-terminated silanols. However, a disadvantage of these unsubstituted cyclic silazanes is that they can be synthesized only in very poor yields or by starting with expensive starting materials. The syntheses frequently employ very toxic allylamine, whose use is subject to particularly strict safety precautions.

Of greater interest is the synthesis of N-substituted silazanes which can frequently be prepared in better yields. However, if the N-silyl-substituted silazane described in U.S. Pat. No. 3,146,250 is used, the reaction with hydroxy-terminated siloxanes gives undesired by-products as indicated in the following reaction scheme

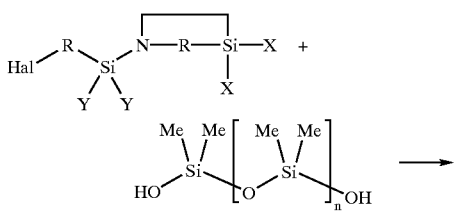

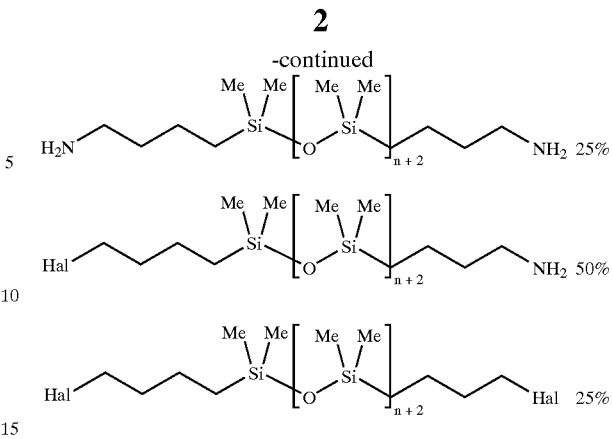

In these formulae, Y and X are, for example, methyl, R is propyl, and Hal is halogen, for example chlorine. The proportions of the respective products can be derived from simple probability calculations.

If the N-substituted silazanes of the formula II

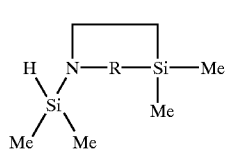

(II)

where R for example, is a propyl group, are used, as described in DE 3546376, undesired by-products are likewise obtained in considerable amounts:

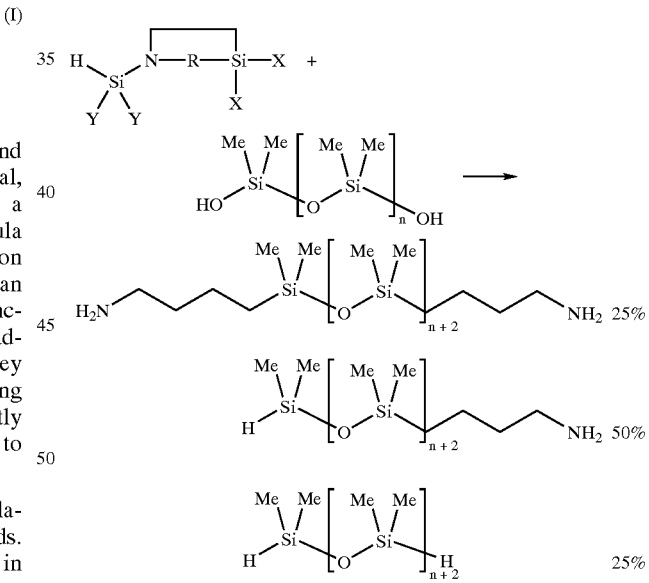

SUMMARY OF THE INVENTION

The invention provides a process for preparing an amino-functional organosiloxanes of the formula III,

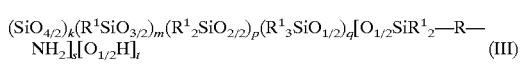

(III)

which comprises reacting an organosiloxane of the formula IV

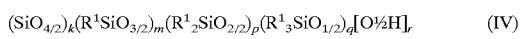

(IV)

with a cyclic silazane of the formula V

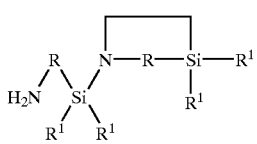
(V)

where
- R is a divalent Si—C—and C—N—bonded, unsubstituted or cyano- or halogen-substituted $C_3$–$C_{15}$-hydrocarbon radical in which one or more non-adjacent methylene units may be replaced by —O—, —CO—, —COO—, —OCO— or —OCOO—, —S— or —NR$^x$—groups and in which one or more non-adjacent methine units may be replaced by —N =, —N =N— or —P= groups, where at least 3 and not more than 6 atoms are located between the silicon atom and the nitrogen atom of the ring,
- R$^x$ is hydrogen or a $C_1$–$C_{10}$-hydrocarbon radical which may be unsubstituted or substituted by —CN or halogen,
- R$^1$ is a hydrogen atom or a monovalent Si—C—bonded $C_1$–$C_{20}$-hydrocarbon radical which may be unsubstituted or substituted by —CN, —NCO, —NR$^x_2$, —COOH, —COOR$^x$, -halogen, -acryl, -epoxy, —SH, —OH or —CONR$^x_2$ or is a $C_1$–$C_{15}$-hydrocarbonoxy radical in which one or more non-adjacent methylene units may be replaced by —O—, —CO—, —COO—, —OCO— or —OCOO—, —S— or —NR$^x$— groups and in which one or more non-adjacent methine units may be replaced by —N =, —N =N— or —P = groups,
- s is at least 1,
- r is at least 1,
- s+t is equal to r and
- k+m+p+q is at least 2.

The cyclic silazanes of the formula V used can be prepared simply and in high yields. In addition, they react with hydroxy-functional siloxanes of the formula IV without use of special catalysts and without the formation of by-products.

In the cyclic silazane of the formula V, R may be aliphatically saturated or unsaturated, aromatic, linear or branched. R is preferably an unbranched $C_3$–$C_6$-alkylene radical which may be substituted by halogen atoms, in particular fluorine and chlorine. It is preferred that 3 atoms are located between the silicon atom and the nitrogen atom of the ring.

The $C_1$–$C_{20}$-hydrocarbon radicals and $C_1$–$C_{20}$-hydrocarbonoxy radicals R$^1$ may be aliphatically saturated or unsaturated, aromatic, linear or branched. R$^1$ preferably has from 1 to 12 atoms, in particular from 1 to 6 atoms, preferably only carbon atoms, or one alkoxy oxygen atom and otherwise only carbon atoms. R$^1$ is preferably a linear or branched $C_1$–$C_6$-alkyl radical. Particular preference is given to the radicals methyl, ethyl, phenyl, vinyl, and trifluoropropyl.

Preference is given to preparing the compounds of the formula III in which R is a propylene radical and R$^1$ is methyl, ethyl, phenyl, vinyl or trifluoropropyl.

The amino-functional organosiloxane of the formula III can be linear, cyclic or branched. The sum of k, m, p, q, s and t is preferably in the range from 2 to 20,000, in particular from 8 to 1000. To make a reaction between the organosiloxane of the formula IV and the silazane possible, r has to be >0, i.e. the organosiloxane of the formula IV must contain hydroxy groups.

Preferred variants of branched organosiloxanes of the formula III are organosilicone resins. These may comprise a plurality of units, as indicated in the formula III, with the molar percentages of the units present being given by the indices k, m, p, q, r, s and t. The proportion of units r is preferably from 0.1 to 20%, based on the sum of k, m, p, q and r. At the same time, k+m also must be >0. In the case of organosiloxane resins of the formula III, s must be >0 and s+t must be equal to r.

Preference is given to resins in which 5% <k+m <90%, based on the sum of k, m, p, q, r, s and t, and t is preferably 0. In a particularly preferred case, the radical R is a propylene radical and R$^1$ is a methyl radical.

If resins which have a specified amine content are to be prepared, the stoichiometric ratio of resin to cyclic silazane is selected so that the desired amine content is achieved. Remaining Si—OH groups may, if appropriate, remain unreacted in the product.

A further preferred variant of an amino-functional organosiloxanes of the formula III is a linear organosiloxane of the formula VI,

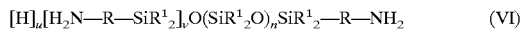
(VI)

which is prepared from an organosiloxane of the formula VII

(VII)

by reaction with a cyclic silazane of the formula V above, where
- u is 0 or 1,
- v is 1−u and
- n is from 1 to 20,000, and wherein
- u is preferably 0, and
- n is preferably from 1 to 20,000, in particular from 8 to 2000.

If a mixture of starting compounds of the formula VII is used, the value of n is the average degree of polymerization of the silanols of the formula VII present.

The linear organosiloxanes of the formula VI prepared in this way can be characterized essentially by 3 different parameters:
-viscosity (or molecular weight)
-amine content
-degree of amino-functionality of the end groups.
However, only two of these parameters can be varied independently in the case of a linear organosiloxane of the formula VI, i.e. at a given viscosity and functionality the amine content is fixed. At a given amine content and viscosity, the functionality is fixed, and in the case of a given amine content and functionality, the viscosity is fixed.

If a linear organosiloxane of the formula VI in which the degree of functionalization plays no role, i.e. in the case of silicone oils not required to have a functionality of 2, but instead defined only by the total amine content and viscosity, a suitable organosiloxane of the formula VII which gives the end product the desired viscosity is chosen as the silicone component and functionalization is achieved using a cyclic silazane of the formula V in an amount corresponding to the amine content of the final product.

The compounds of the formula VI have the further advantage that they can, when u >0, be condensed either with themselves or with compounds of the formula VII, if necessary with the aid of a catalyst, to give further compounds of the formula VI which, however, have a higher molecular weight, i.e. the numerical value of n increases. In a particularly preferred case, n is from 15 to 50 before the condensation and from 50 to 2000 after the condensation.

In the process for preparing an amino-functional organosiloxane of the formula III, the amount of silazanes of the formula V used depends on the number of silanol groups to be functionalized. However, if complete functionalization of the OH groups is to be achieved, the silazane is added in at least equimolar amounts. If the cyclic silazane is used in excess, the unreacted silazane can subsequently be distilled off again or hydrolyzed and then, if appropriate, removed.

The process is preferably carried out at from 0° C. to 100° C., more preferably from 10° C. to 40° C. The process can be carried out in suitable reactors either in the presence of solvents or without the use of solvents. The reaction can be carried out under subatmospheric pressure, under superatmospheric pressure or at atmospheric pressure (0.1 MPa).

When using solvents, preference is given to inert solvents, in particular to aprotic solvents such as aliphatic hydrocarbons, i.e. heptane or decane, and to aromatic hydrocarbons, i.e. toluene or xylene. Ethers such as THF, diethyl ether or MTBE can likewise be used. The amount of solvent should be sufficient to ensure sufficient homogenization of the reaction mixture. Solvents or solvent mixtures having a boiling point or boiling range up to 120° C. at 0.1 MPa are preferred.

If a deficiency of the silazane of the formula VI is added to the organosiloxane of the formula IV, remaining unreacted Si—OH groups can remain in the amino-functional organosiloxane of the formula III or may be reacted with other silazanes of the formula VIII:

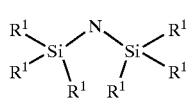    (VIII)

This reaction provides an amino-functionalized organosiloxane of the formula IX

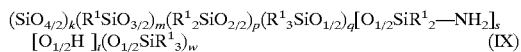    (IX)

Here, R, $R^1$, k, m, p, q and s are as defined above; t is greater than or equal to 0; w is greater than 0; and s+t+w=r, with r being as defined in formula IV above. Silazanes of the formula VIII can be introduced simultaneously with the cyclic silazane of the formula V or after reaction of the silazane of the formula V.

Amino-functional organosiloxanes of the formula IX which have been prepared by reaction of silazanes of the formula VIII with a cyclic silazane of the formula V can, for example, be used for increasing the amine number of highly viscous aminosilicones. This gives mixtures of aminosilicones and aminosilicone resins which combine a high amine number with a high viscosity. This is a combination which cannot be achieved when using pure bifunctional aminosilicones.

Reaction of linear organosiloxanes of the formula VII above with both silazanes of the formula V and silazanes of the formula VIII gives compounds of the formula X

    (X)

where $R^1$, R and n are as defined above and, on average, u >0, v <1 and u+v=1. This second termination may be dispensed with, but offers significant advantages in respect of the stability of the materials at elevated temperatures, since Si—OH groups tend to condense at relatively high temperatures and thus increase the viscosity of the resulting solutions.

A silazane of the formula V can be prepared by a process in which a haloalkyldialkylchlorosilane of the formula XI

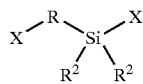

or a bis(haloalkyl)tetraalkyldisilazane of the formula XII

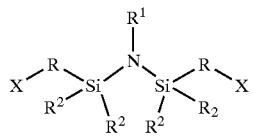

or a mixture of compounds of the formulae XI and XII, where

X is F, Cl, Br or I, $R^2$ is as defined for $R^1$ and $R^1$ and R are as defined above, is reacted with ammonia, preferably under superatmospheric pressure.

It should be noted that the meanings of all the symbols in the above formulae are independent of one another.

In the following examples, all percentages are by weight, all pressures are 0.10 MPa (abs.) and all temperatures are 20° C. unless indicated otherwise.

EXAMPLE 1

1000 g of Me-siloxane (bishydroxy-terminated polydimethylsiloxane having a mean molecular weight of 3000 g/mol) were reacted at room temperature with 84.8 g of N-((3-aminopropyl)dimethylsilyl)-2,2-dimethyl-1-aza-2-silacyclopentane. $^1$H-NMR and $^{29}$Si—NMR showed that after 3 hours all OH groups had been converted into aminopropyl units and residual N-((3-aminopropyl) dimethylsilyl)-2,2-dimethyl-1-aza-2-silacyclopentane was present. To react the remaining silazane, 2 ml of water were subsequently added to the reaction solution and the solution was briefly distilled at 60° C. under reduced pressure (20 mbar).

EXAMPLE 2

1000 g of Me-siloxane (bishydroxy-terminated polydimethylsiloxane having a mean molecular weight of 3000 g/mol) were reacted at room temperature with 77.2 g of N-((3-aminopropyl)dimethylsilyl)-2,2-dimethyl-1-aza-2-silacyclopentane. $^1$H-NMR and $^{29}$Si—NMR showed that after 2 hours all OH groups had been converted into aminopropyl units and no residual N-((3-aminopropyl) dimethylsilyl)-2,2-dimethyl-1-aza-2-silacyclopentane could be detected.

EXAMPLE 3

100 g of silicone oil (bishydroxy-terminated polydimethylsiloxane having a mean molecular weight of 13,000 g/mol) were reacted at 50° C. with 1.8 g of N-((3-aminopropyl)dimethylsilyl)-2,2-dimethyl-1-aza-2-silacyclopentane. $^1$H-NMR and $^{29}$Si—NMR showed that after 2 hours all OH groups had been converted into aminopropyl units and no residual N-((3-aminopropyl) dimethylsilyl)-2,2-dimethyl-l-aza-2-silacyclopentane could be detected.

EXAMPLE 4

100 g of silicone oil (bishydroxy-terminated polydimethylsiloxane having a mean molecular weight of 28,000 g/mol) were reacted at 50° C. with 0.85 g of N-((3-aminopropyl)dimethylsilyl)-2,2-dimethyl-1-aza-2-silacyclopentane. $^1$H-NMR and $^{29}$Si—NMR showed that after 2 hours all OH groups had been converted into aminopropyl units and no residual N-((3-aminopropyl) dimethylsilyl)-2,2-dimethyl-1-aza-2-silacyclopentane could be detected.

EXAMPLE 5

100 g of silicone oil (bishydroxy-terminated polydiphenylsiloxane having a mean molecular weight of 1000 g/mol) were reacted at 100° C. with 23.2 g of N-((3-aminopropyl)dimethylsilyl)-2,2-dimethyl-1-aza-2-silacyclopentane. $^1$H—NMR and $^{29}$Si—NMR showed that after 2 hours all OH groups had been converted into aminopropyl units and no residual N-((3-aminopropyl)dimethylsilyl)-2,2-dimethyl-1-aza-2-silacyclopentane could be detected.

EXAMPLE 6

1000 g of silicone oil (bishydroxy-terminated polymethylvinylsiloxane having a vinyl:methyl ratio of 1:4 and a mean molecular weight of 2800 g/mol) were reacted at room temperature with 83.4 g of N-((3-aminopropyl) dimethylsilyl)-2,2-dimethyl-1-aza-2-silacyclopentane. $^1$H—NMR and $^{29}$Si—NMR showed that after 3 hours all OH groups had been converted into aminopropyl units and no residual N-((3-aminopropyl)dimethylsilyl)-2,2-dimethyl-1-aza-2-silacyclopentane could be detected.

EXAMPLE 7

1000 g of silicone oil (bishydroxy-terminated polymethylvinylsiloxane having a vinyl:methyl ratio of 1:12 and a mean molecular weight of 2600 g/mol) were reacted at room temperature with 88.9 g of N-((3-aminopropyl) dimethylsilyl)-2,2-dimethyl-1-aza-2-silacyclopentane. $^1$H—NMR and $^{29}$Si—NMR showed that after 3 hours all OH groups had been converted into aminopropyl units and no residual N-((3-aminopropyl)dimethylsilyl)-2,2-dimethyl-1-aza-2-silacyclopentane could be detected.

EXAMPLE 8

100 g of silicone oil (bishydroxy-terminated polymethyltrifluoropropylsiloxane having a trifluoropropyl:methyl ratio of 1:1 and a mean molecular weight of 900 g/mol) were reacted at room temperature with 25.8 g of N-((3-aminopropyl)dimethylsilyl)-2,2-dimethyl-1-aza-2-silacyclopentane. $^1$H—NMR and $^{29}$Si—NMR showed that after 3 hours all OH groups had been converted into aminopropyl units and no residual N-((3-aminopropyl) dimethylsilyl)-2,2-dimethyl-1-aza-2-silacyclopentane could be detected.

What is claimed is:

1. A process for preparing an amino-functional organosiloxane of the formula III,

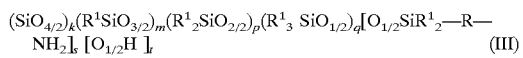

which comprises reacting an organosiloxane of the formula IV

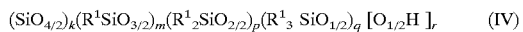

with a cyclic silazane of the formula V

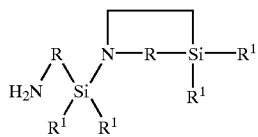

where

R is a divalent Si—C— and C—N—bonded, unsubstituted or cyano- or halogen-substituted $C_3$–$C_{15}$-hydrocarbon radical in which one or more non-adjacent methylene units are optionally replaced by —O—, —CO—, —COO—, —OCO— or —OCOO—, —S— or —NR$^x$— groups and in which one or more non-adjacent methine units are optionally replaced by —N=, —N=N— or —P=groups, where at least 3 and not more than 6 atoms are located between the silicon atom and the nitrogen atom of the ring, $R^x$ is hydrogen or a $C_1$–$C_{10}$-hydrocarbon radical which may be unsubstituted or substituted by —CN or halogen, $R^1$ is a hydrogen atom or a monovalent Si—C-bonded $C_1$–$C_{20}$-hydrocarbon radical which may be unsubstituted or substituted by —CN, —NCO, —NR$^x_2$, —COOH, —COOR$^x$, -halogen, -acryl, -epoxy, —SH, —OH or —CONR$^x_2$ or is a $C_1$–$C_{15}$-hydrocarbonoxy radical in which one or more non-adjacent methylene units are optionally replaced by —O—, —CO—, —COO—, —OCO— or —OCOO—, —S— or —NR$^x$— groups and in which one or more nonadjacent methine units may be replaced by —N=, —N=N— or —P=groups, s is at least 1, r is at least 1, s+t is equal to r and k+m+p+q is at least 2.

2. The process of claim 1, wherein R is an unbranched $C_3$–$C_6$-alkylene radical which may be substituted by halogen atoms.

3. The process of claim 1, wherein $R^1$ is methyl, ethyl, phenyl, vinyl or trifluoropropyl.

4. The process of claim 2, wherein $R^1$ is methyl, ethyl, phenyl, vinyl or trifluoropropyl.

5. The process of claim 1, wherein the sum of k, m, p, q, s and t is from 2 to 20,000.

6. The process of claim 1, wherein resins in which 5%<k+m<90%, based on the sum of k, m, p, q, r, s and t, are prepared.

7. The process of claim 1, wherein a linear organosiloxane of the formula VI,

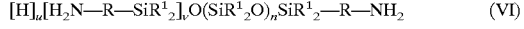

is prepared by reacting an organosiloxane of the formula VII

with a cyclic silazane of the formula V, where u is 0 or 1, v is 1–u, and n is from 1 to 20,000.

8. The process of claim 1, which is carried out at a temperature of from 0° C. to 100° C.

9. The process of claim 1, wherein an amino-functional organosiloxane of the formula IX

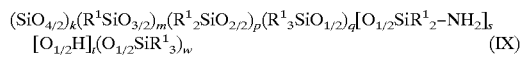

is prepared by adding a deficiency of the silazane of the formula V to the organosiloxane of the formula IV and reacting unreacted Si—OH groups in the resulting amino-functional organosiloxane of the formula III with silazanes of the formula VIII,

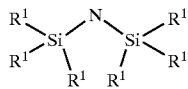

(VIII)

where
  t is greater than or equal to 0,
  w is greater than 0, and
  s+t+w=r.

10. The process as claimed in claim 9, wherein silazanes of the formula VIII are introduced after the reaction of the silazane of the formula V.

* * * * *